(12) United States Patent
Bartlett

(10) Patent No.: US 7,987,303 B2
(45) Date of Patent: Jul. 26, 2011

(54) MEDICAL INTERFACE WITH MULTIPLE COMMUNICATION CHANNELS HAVING DIFERENT DATA RATES WHEREIN ONE CHANNEL IS ALWAYS ACTIVE

(75) Inventor: Stewart Gavin Bartlett, Torrensville (AU)

(73) Assignee: Signostics Limited, Therazton (AT)

( * ) Notice: Subject to any disclaimer, the term of this patent is extended or adjusted under 35 U.S.C. 154(b) by 241 days.

(21) Appl. No.: 12/305,975

(22) PCT Filed: Jun. 29, 2007

(86) PCT No.: PCT/AU2007/000902
§ 371 (c)(1),
(2), (4) Date: Dec. 22, 2008

(87) PCT Pub. No.: WO2008/003126
PCT Pub. Date: Jan. 10, 2008

(65) Prior Publication Data
US 2010/0240991 A1    Sep. 23, 2010

(30) Foreign Application Priority Data
Jul. 7, 2006   (AU) ............................... 2006903662

(51) Int. Cl.
*G06F 15/16* (2006.01)
*G06F 13/00* (2006.01)
*G06F 15/177* (2006.01)
*A61B 8/00* (2006.01)
*A61B 1/04* (2006.01)

(52) U.S. Cl. .................... 710/62; 710/8; 710/9; 710/10; 710/11; 710/16; 600/300; 600/459; 600/437; 607/34

(58) Field of Classification Search ............... 710/8–10, 710/305; 600/300, 459; 607/34
See application file for complete search history.

(56) References Cited

U.S. PATENT DOCUMENTS

| | | | | |
|---|---|---|---|---|
| 5,839,094 | A * | 11/1998 | French ............................. | 702/91 |
| 6,381,557 | B1 | 4/2002 | Babula et al. | |
| 6,650,942 | B2 * | 11/2003 | Howard et al. .................. | 607/34 |
| 7,048,687 | B1 * | 5/2006 | Reuss et al. ..................... | 600/300 |
| 7,162,307 | B2 * | 1/2007 | Patrias ............................ | 607/60 |
| 2006/0161054 | A1 * | 7/2006 | Reuss et al. ..................... | 600/300 |
| 2006/0288147 | A1 * | 12/2006 | Hsieh ............................. | 710/305 |
| 2007/0004342 | A1 | 1/2007 | Kasprzyk et al. | |
| 2007/0239019 | A1 * | 10/2007 | Richard et al. ................. | 600/459 |

FOREIGN PATENT DOCUMENTS
WO        02/098507 A2     12/2002

* cited by examiner

*Primary Examiner* — Tammara Peyton

(57) ABSTRACT

An ultrasound measurement system including a handheld display and processing means, an ultrasound transducer, a processing means of a substantially similar weight to the handheld display and processing means, and a transmission cable interconnecting the handheld display and processing means with the ultrasound transducer and processing means, the cable being of sufficient length to provide a means to mechanically locate the system around the neck of a user.

10 Claims, 10 Drawing Sheets

ND CHANNEL IS ALWAYS ACTIVE

FIELD OF THE INVENTION

The present invention relates to the field of communication interface systems, particularly to an interface suitable for portable medical equipment.

BACKGROUND OF THE INVENTION

A large variety of medical devices exist in the market. Many of these medical devices include the connection of sensors or probes to a host processing system. Examples include ultrasound platforms, ECG machines, critical care monitors, and emergency care monitors. The interfaces for these connections are usually proprietary using different electrical standards, protocols, and connectors.

Some companies produce products with an interface which allows different probes or pods or sensor units to be connected. One example is the range of critical care monitors from Draeger Medical, where various probes or pods can be connected to the monitor. The probes or pods connect to the monitor through a cable providing power and communications. Usually, communications are via a standard interface such as RS232. The critical care monitors can connect to pods or probes such as CO2 monitoring, EEG monitoring, ECG monitoring, blood pressure monitoring, and oxygen saturation monitoring. The data rate required for monitoring all of these conditions is relatively low (orders of Kbytes per second), and adequately served by standard interfaces such as RS232. However, this connection scheme cannot support pod functions requiring higher transfer rates such as ultrasound, or camera based pod functions such as endoscopes.

There are a variety of interfaces used to connect ultrasound probes to host processing systems. The most common interface is an analog interface, where raw analog voltages are transmitted to and from probe ceramics using a cable and connector. The number of channels in most ultrasound systems is very high, resulting in cables and connectors interfacing large numbers of channels. The connectors and interfaces for these ultrasound systems are proprietary, with no industry accepted standard.

A more recent development is where an ultrasound pod connects to an ultrasound probe, and the pod then connects to a host processing system. The link between the pod and the host must support very high data rates, as even a single channel of raw digital data from an ultrasound probe uses a bandwidth which may exceed 300 Mbps. Terason Corporation market such a product, where the pod to host system link is via a Firewire (IEEE1394) interface. Other manufacturers interface to digital probes using USB2.0 interfaces. These standards operate at data rates of up to 480 Mbps.

A significant disadvantage of using a USB2 or a Firewire interface is relatively high power consumption. For example, a standard USB2 host device such as the ISP1760 made by Philips, consumes approximately 254 mW when in operation. A client USB2 device containing a slave USB2 controller such as the ISP1583 consumes about 198 mW in operation. Therefore, the communications overhead for a USB2 device is approximately 452 mW. This power consumption is a significant problem for portable devices reliant on battery power, or other applications where low overall power consumption is important.

The USB mechanical standard does not provide an interface particularly well suited to a handheld or portable medical device. The USB2 standard specifies a maximum extraction force for a USB2 connector to be 10N, and therefore is not suited to being used in handheld devices where large stresses may be place on connectors and cables.

It is an object of the present invention to provide a medical device connector and interface that overcomes or at least substantially ameliorates the problems associated with the prior art.

SUMMARY OF THE INVENTION

The invention provides an interface method particularly well suited to medical connections, especially connections to and from handheld devices.

In one form of the invention, it may be said to lie in an interface system adapted to provide a communications interface between a processing unit and one or more sensor units including a first interface termination unit in direct electrical contact with the processing unit, a second interface termination unit associated with the sensor unit; a message channel being a communications channel adapted to carry message data at a first data rate between the processing unit and the sensor unit, said message channel being active at least at substantially all times that the processing unit is active, a data channel being a communications channel adapted to carry sensor data at a second data rate connecting the first and second interface termination units; said data channel being active substantially only when sensor data is required to be transmitted from the sensor unit to the processing unit; said second data rate being substantially greater than said first data rate.

In preference there are further included at least one pair of connectors adapted to provide a removable connection for conductors carrying the said message and data channels.

In preference the first interface termination unit is adapted to be reconfigured in use to use a communication protocol and data rate appropriate for the sensor unit, this reconfiguration being triggered by information received from the sensor unit via the message channel.

In preference the first interface termination unit is reconfigured by the processing unit.

In preference data required to reconfigure the first interface termination unit is provided from the sensor unit.

In a further form, the invention may be said to lie in a method of providing an interface between a processing unit and a sensor unit including the steps of providing a message channel being a communications channel adapted to carry message data between the sensor unit and the processing unit at a first data rate, said message channel being active at substantially all times that the processing unit is active, providing a data channel being a communications channel adapted to carry sensor data between the sensor unit and the processing unit at a second data rate; said data channel being active substantially only when sensor data is required to be transmitted from the sensor unit to the processing unit; said second data rate being substantially greater than said first data rate, the processing unit interrogating the sensor unit via the message channel as to the configuration of the data channel required by the sensor unit for communication of sensor data to the processing unit, the processing unit reconfiguring parameters of the data channel to accord with the requirements of the sensor unit.

In preference a plurality of sensor units, each with a different function are provided, and the message and data channels are adapted to be removably connected between the processing unit and the particular sensor unit in use at a given time.

In preference the sensor unit is a medical diagnostic probe.

In preference the sensor unit is selected from an ultrasound transducer, an endoscope, an auscultation transducer, and an otoscope.

In preference the interface further includes electrical connections adapted to connect electrical wires carrying the message and data channels, and an optical fibre connector adapted to connect optical fibres carrying an optical image to the image sensor.

In a further form, the invention may be said to reside in a connector for use with the interface system described including electrical connections adapted to connect electrical wires carrying the message and data channels, and a waveguide connector adapted to connect a rigid or semi-rigid waveguide to the image sensor.

Other objects and advantages of the present invention will become apparent from the following description, taken in connection with the accompanying drawings, wherein, by way of illustration and example, an embodiment of the present invention is disclosed.

BRIEF DESCRIPTION OF THE DRAWINGS

A preferred embodiment of the invention will now be described, by way of example only, with reference to the accompanying drawings in which.

DESCRIPTION OF PREFERRED AND OTHER EMBODIMENTS

Figure 1:
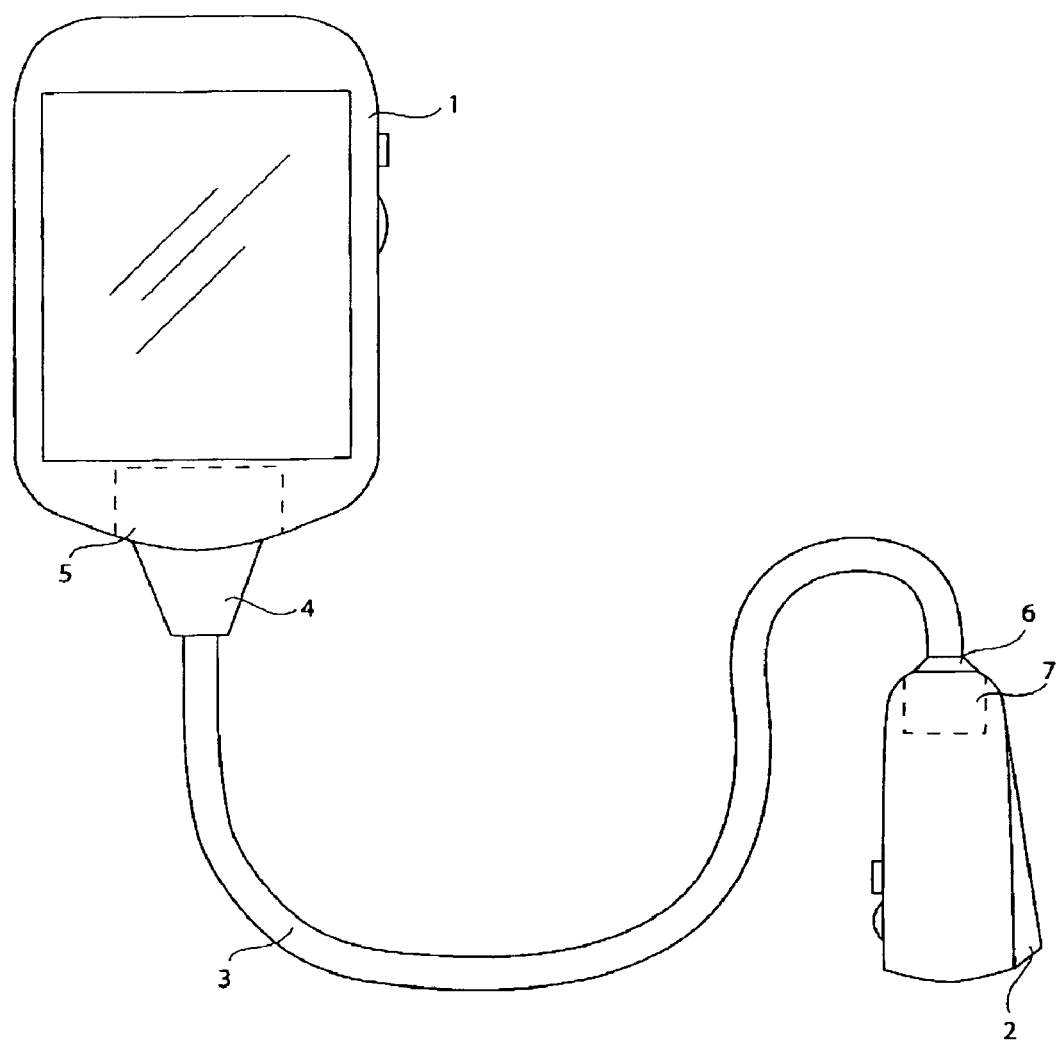
FIG. 1 is an illustration of a medical diagnostic system employing an embodiment of the interface system

Now referring to FIG. 1, a preferred embodiment includes a host system 1 connected to a sensor unit 2 by way of connection cord 3 and host end plug connector 4 and sensor end plug connector 6. Either or both of these plug connectors may be absent.

The sensor unit includes a probe or sensor or transducer and a processing unit. This may be, for example, an ultrasound transducer, an auscultation transducer or any other scanning or detection device. The interface of the invention is employed to communicate information about the sensor unit, and data gathered by the sensor unit to the host system.

In general, sensor units providing different functionality may be connected to the host system. The host system is able to identify a required interface method, protocol and data rate for communication with the sensor unit. The host is then able to modify communication parameters in order to receive sensor data communication from the sensor unit.

The host system provides display, analysis and storage of data gathered by the sensor unit.

The host system can support a variety of serial data interface protocols and speeds. The interface to the host contains a programmable interface unit 5, and is able to be configured according to the communication protocol and speed required by the specific sensor unit which is connected to the host unit.

The different sensor units will have differing requirements as to the nature and speed of the data which will need to be communicated to the host. The sensor unit includes an interface termination unit 7 which allows negotiation with the host as to the communication parameters required.

Figure 2:
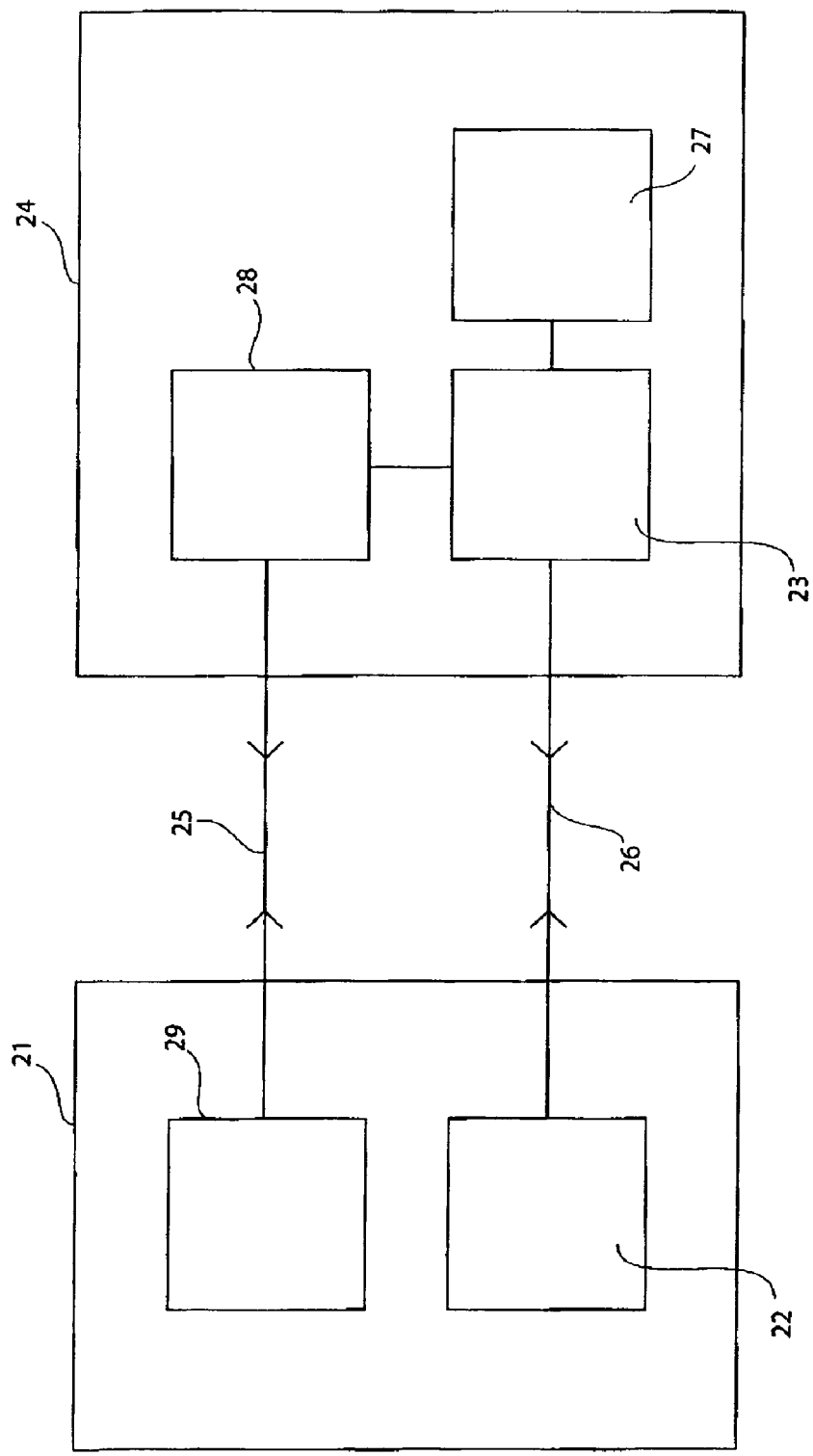
FIG. 2 shows a block diagram illustrating an embodiment of the invention in use with a host system.

FIG. 2 shows a block diagram of a preferred embodiment wherein there is a host processor 21 connected to sensor unit 24. The connection interface includes a low speed message channel 25 and a high speed data channel 26.

The host unit includes a data processing unit 29 and a host interface termination unit 22. The sensor unit 24 includes a sensor unit processor 28 and a sensor interface termination unit 23. The sensor unit also includes a probe or sensor or transducer 27.

The message channel 25 is a low speed, low power, always on connection. Since different sensor units, with different data channel communication parameters may be plugged to the host unit, it is necessary to have a method for communicating these parameters to the host processor, independently of the main data communication channel. This function is supplied by the message channel.

At power up or at the time when a sensor unit is plugged in to the host unit, the sensor unit initiates negotiation with the host system, via the message channel. The host system negotiates data channel parameters with the sensor unit, and then configures the host interface termination unit 23 to be compatible with the sensor unit data channel parameters. In the preferred embodiment, the host interface termination unit is a field-programmable gate array (FPGA).

The interface is especially useful in handheld or portable devices which rely on battery power. The message channel is always active or open, and therefore must have very low static power consumption if acceptable battery life is to be achieved. Essentially, when the message channel is not being used, the power consumption must be very low.

The message channel preferably operates as a multi-master bus. A multi-master bus allows either end of the bus to be in a low power sleep or suspend state, and for the other end to activate the bus and bring the first end out of the low power sleep or suspend state. In a preferred embodiment an I2C bus is used to implement the message channel. The I2C bus can operate in multi-master mode, with many microcontrollers and microprocessors incorporating I2C functionality. Other bus architectures with low static power consumption may be used. Such architectures may include wireless architectures.

The data channel 26 provides a data link between sensor units and the host. The configuration can vary according to the type of sensor unit connected and the data transmission rate required for the sensor unit. Some sensor units such as blood testing probes may only require extremely low transmission rates, and in these circumstances the data channel may never be used. Other systems such as audio based probes may require moderate data rates, and in these cases the data channel can be configured to support a moderate data transmission rate. Yet other sensor units such as incorporating imaging probes may require high data rates, and the data channel can be configured to support a high data rate.

The data channel preferably uses a differential signalling technique, enabling a system with high reliability, excellent noise immunity, low power consumption, and low RF noise output or emissions. The preferred embodiment uses low voltage differential signalling (LVDS), which supports data rates up to 600 MBits/second. Where faster data rates are required, the data channel may be implemented using a fibre optic link. Single mode fibre optic links can support data rates up to 40 GBits/second. Any other bus system able to be supported by the host system and the sensor unit may be used to implement the data channel. A wireless link may also be used to implement the data channel. Such a wireless link may be implemented using any available wireless communication protocol, including but not limited to Bluetooth and 802.11.

The sensor unit termination unit 23 will usually be pre-configured with the protocol and data rate required for operation. The sensor termination unit is configurable, being implemented as a field programmable gate array (FPGA) in a preferred embodiment. This means it is possible for the protocol or data rate to be reconfigured. This would most likely occur when the sensor unit is being field upgraded.

In general use, the protocol and data rate required by the sensor unit are fixed or able to be chosen from a group of fixed parameters. The sensor unit is adapted to communicate these requirements to the host processor via the message channel.

Figure 3:
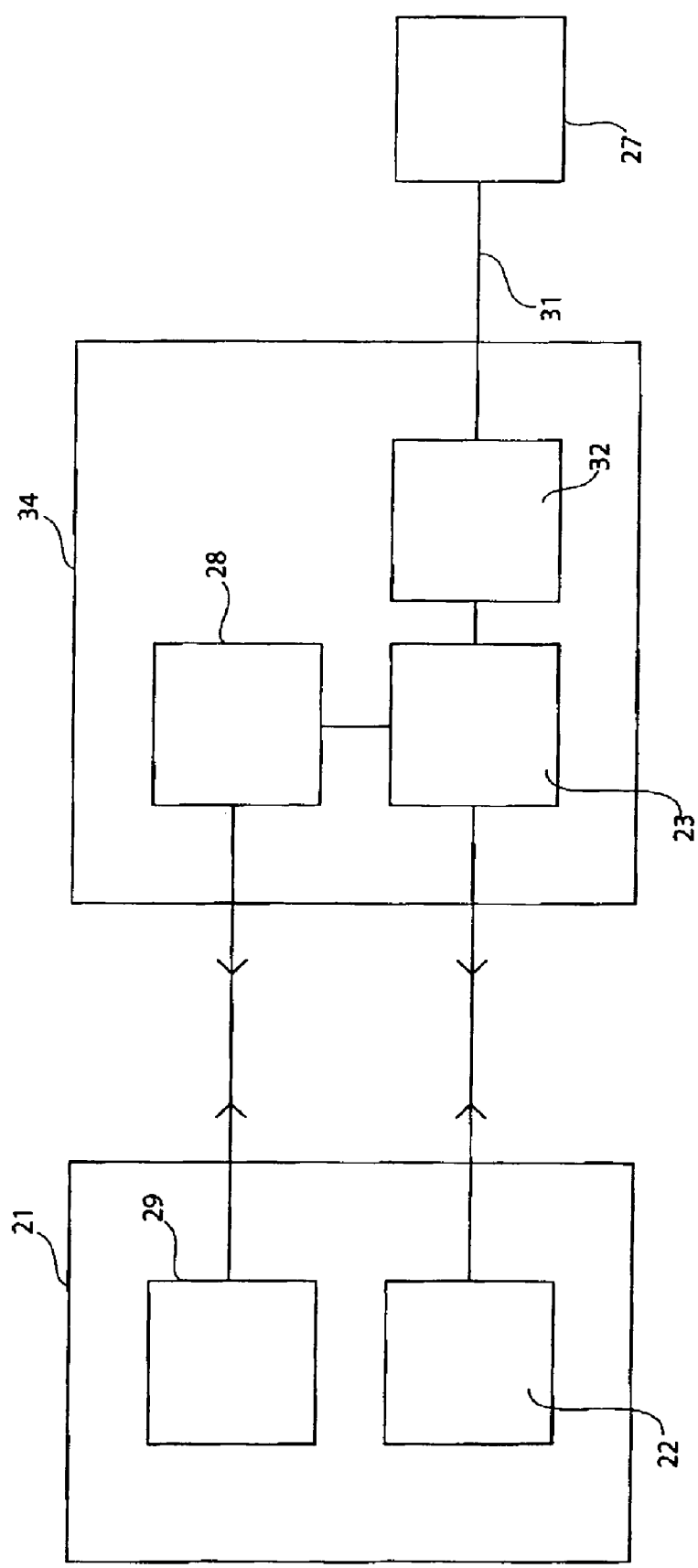
FIG. 3 shows a block diagram of an alternative arrangement illustrating an embodiment of the invention in use with a host system.

In an alternative embodiment, illustrated in FIG. 3, there is a sensor unit 34 which includes a sensor unit processor 28 and a sensor interface termination unit 23. It further includes a probe sensor 32 which is connected to a remote probe 27 by a waveguide 31. This waveguide may be any structure capable of guiding waves generated or received by a probe. In particular, it may be one or more optical fibres, a rigid or semi-rigid optical waveguide, an acoustic waveguide or a microwave waveguide. In the case where an optical waveguide is used, the probe sensor will be an imaging unit, such as a CCD imaging sensor.

Figure 4:
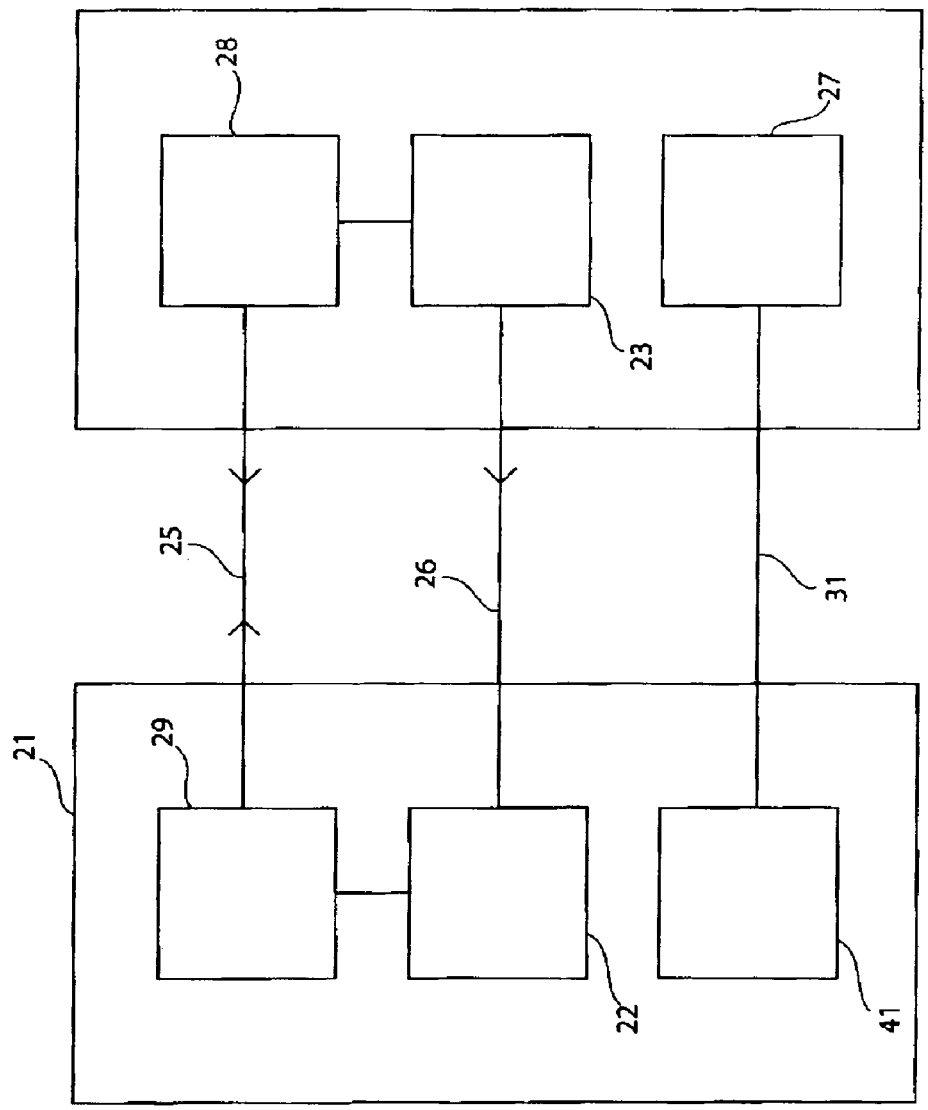
FIG. 4 shows a block diagram of further alternative arrangement illustrating an embodiment of the invention in use with a host system.

In a further embodiment, illustrated in FIG. 4, there is a probe 27, which may be physically incorporated into the sensor unit, or remote from the sensor unit as in the embodiment of FIG. 3. The waveguide 31, connects the probe directly to the host unit, where there is provided a probe sensor 41. The message and data channels are provided and have the same function as in the embodiments described above.

The embodiments of FIG. 3 and FIG. 4 allow the probe to be physically and electrically isolated from the sensor unit electronics. Further, the inclusion of an image receiver provides an interface mechanism for medical probes used to capture images, such as otoscopes, ophthalmoscopes, and endoscopes. With an electrical only system, every sensor unit is required to include an image sensor, whereas with an imaging sensor in the host system the sensor units can be constructed using a waveguide and no image sensor, reducing the cost, size and weight of the sensor unit.

Figure 5:
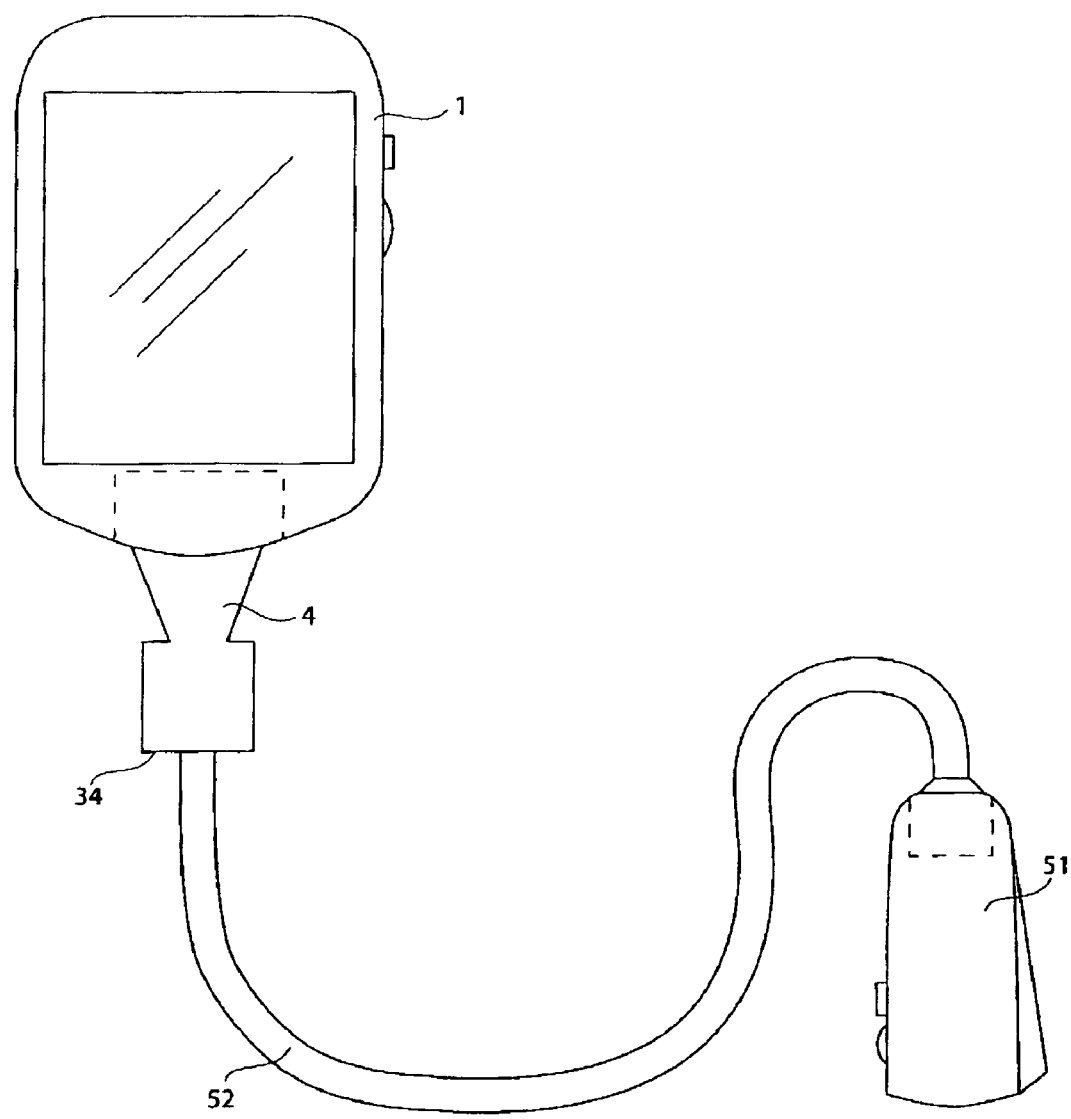
FIG. 5 shows an illustration of a medical diagnostic system employing a further embodiment of the interface system

FIG. 5 shows one alternative physical arrangement of the embodiments of FIG. 3 or FIG. 4. The host unit 1 is connected to the sensor unit 34 directly by connector 4. All of the physical connections for the data and message channel are provided by the connector. A waveguide in the form of an optical fibre connection 52 provides a connection to a probe 51. An image sensor may be located within the sensor unit 34 or the host unit 1. This arrangement allows for the greatest separation between the relatively robust probe and the more sensitive electronic components.

Figure 6:
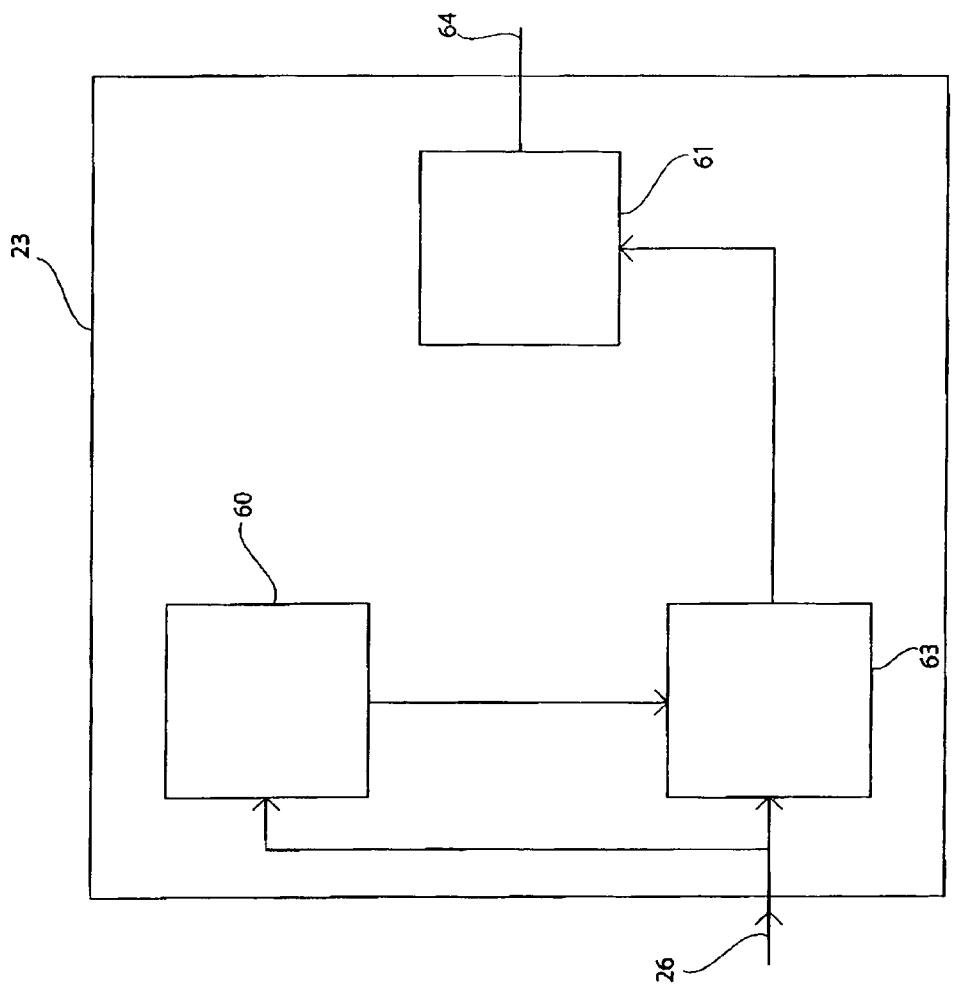
FIG. 6 illustrates a block diagram of a termination unit of an interface of the invention suitable for use with a host processor.

In all illustrated embodiments, the host processor connects to the sensor unit connector via a host termination unit 22, which may be implemented as a field programmable gate array (FPGA). The logical structure of the FPGA is illustrated in FIG. 6. It contains a host processor interface 61, clock recovery circuitry 60, and a data recovery circuit 63.

The host processor communicates with the sensor unit via the data channel and negotiates the required protocol and data transmission rate. If this is not supported by the termination unit, then the host will load a new FPGA configuration file into the FPGA compatible with the negotiated protocol and data rate. The logic modified is usually the clock 60 and data recovery circuitry 63.

These configuration files may be already held in a memory associated with the host unit, or provided by the user, for example, on a memory card, or alternatively automatically uploaded from the sensor unit using the message channel.

A preferred embodiment uses an MSP430 family microcontroller in the sensor unit to implement an I2C message channel. An I2C message channel is a very power efficient mechanism for communicating with the host. The MSP430 family uses as little as 0.1 uA in standby mode, and is able to be activated by any activity of the I2C bus or any other interrupt pin. Even in active mode an MSP430 consumes as lithe as 330 uA. Often a handheld host system and a sensor unit are in a low power state waiting for a user to indicate the system needs to be powered. The sensor unit may automatically detect the system is required for a data acquisition, and will send a wakeup message to the host. The host will wake up, and poll the message channel to determine the state of the sensor unit. The host will then wait for data on the data channel, or perform such other reconfiguration as may be required by the sensor unit.

Other implementations of the message channel are possible. If a wireless channel is to be employed, it must be chosen carefully to ensure that it power consumption, particularly its static power consumption is sufficiently low that adequate battery life can be achieved.

The interface may also further include electrical power connections, enabling the sensor unit to be powered by the host unit.

In a further physical embodiment (not illustrated) both the message channel and the data channel are implemented as wireless channels. Accordingly, there is no physical cabling between the sensor unit and the host unit. Separate battery power must be provided for the host unit and the sensor unit. The host unit in this case may also have a second implementation of the interface, using wired channels, allowing it to accept alternative sensor units which do need to be physically plugged into the host unit.

The interface of the invention is very efficient when compared to prior art communication systems. The interface can configure protocols with little or no communication overhead, as the negotiation of protocol parameters for the data channel takes place only at connection or power-up over a channel independent of the data channel. The data channel protocol is implemented mostly in hardware. As a comparison, USB2 can operate at about 89% efficiency when configured for bulk transfer using large block sizes, that is, when operating in a mode analogous to the data channel. For negotiation or control type messaging, analogous to message channel traffic, USB2 is very inefficient, operating at <10% efficiency with 8 byte payloads. Employing an interface combining a low power message channel and a highly efficient data channel as in the interface of the invention allows optimum power consumption versus performance for all communication circumstances to be approached.

Figure 7:
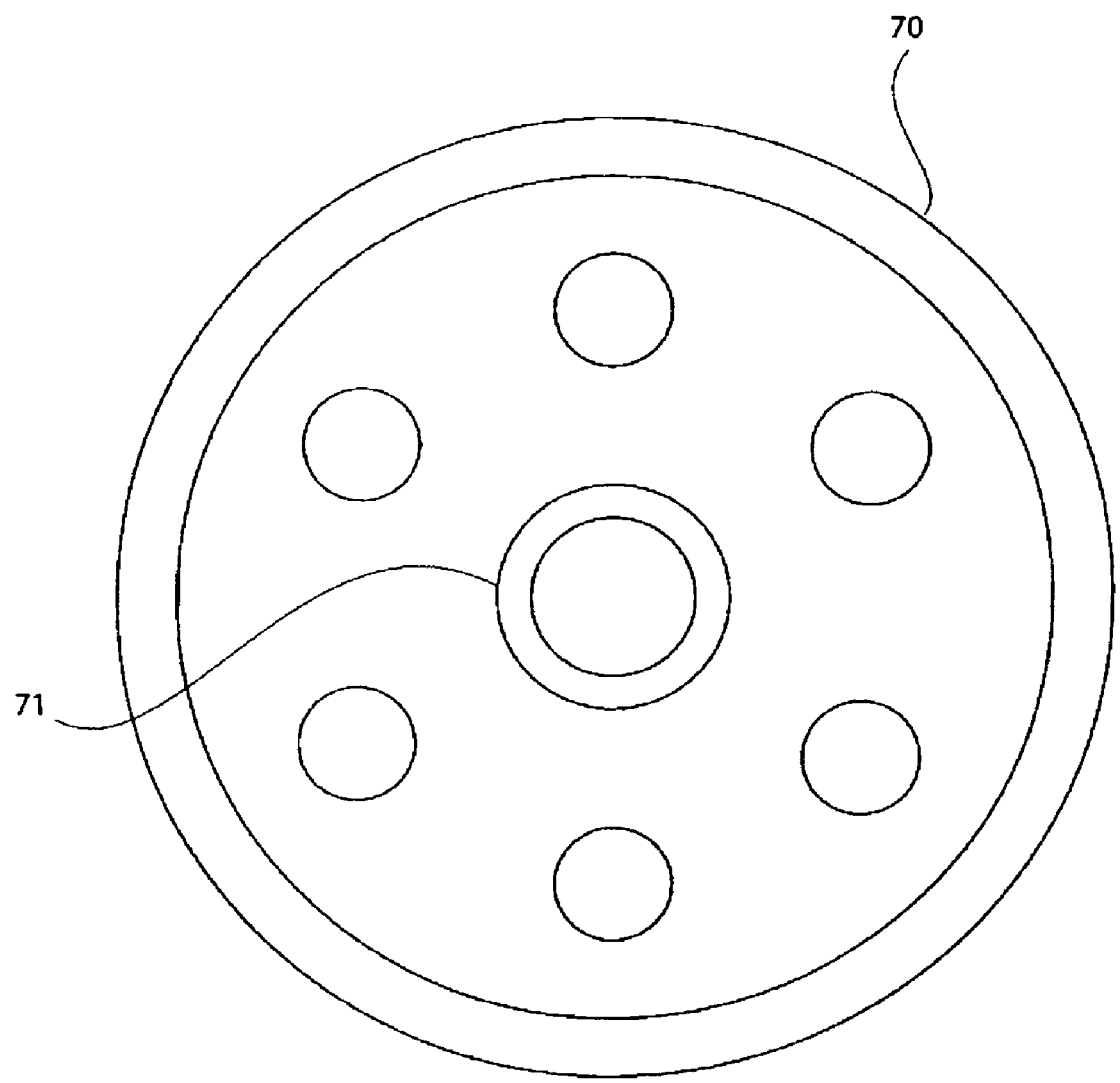
FIG. 7 illustrates a front view of a host connector receptacle of a variation of the preferred embodiment with an added fibre optic interface.

Communications standards such as USB provide connectors of limited strength, with extraction forces as lows as 10N being required to extract the cable. Medical grade connectors such as the miniature Lemo B series or Alden PL-500 series can support above 400N of force, providing a robust and reliable connection for handheld medical products. FIG. 7 illustrates a front view of a medical grade connector with electrical wires 70 and an optical fibre connection 71. A Lemo style push-pull connection is preferred for fibre optic communication systems as it avoids a twisting mechanism to disengage the connection which can damage the fibre-optic glass surface.

Figure 8:
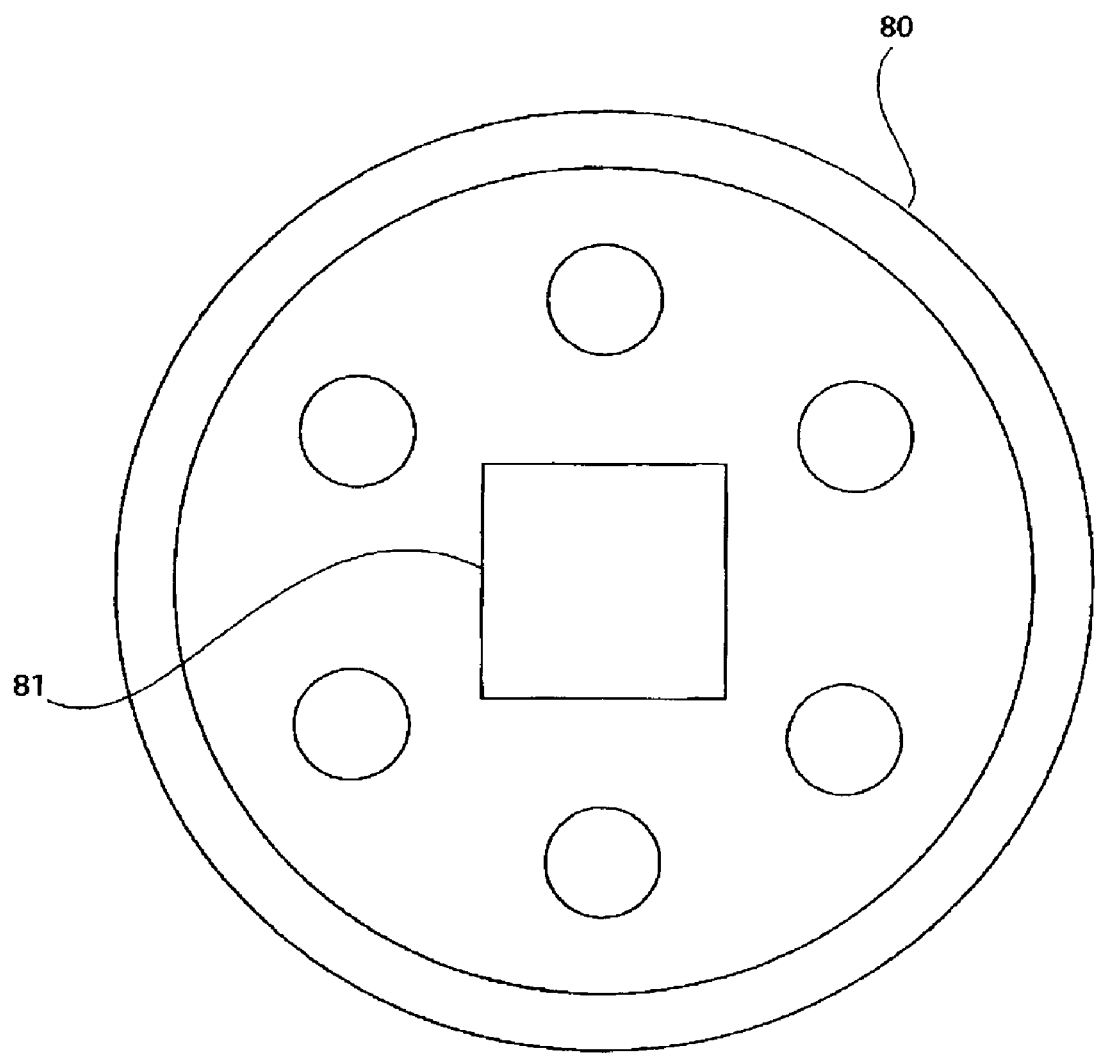
FIG. 8 illustrates a front view of a host connector receptacle with another variation of the preferred embodiment with an added optical waveguide receptacle.

An embodiment of the interface system may include electrical connections and a rigid or semi-rigid waveguide. A possible arrangement of a connector for use with this interface is illustrated in FIG. 8, with electrical connectors 80, and a square waveguide connector 81.

Figure 9:
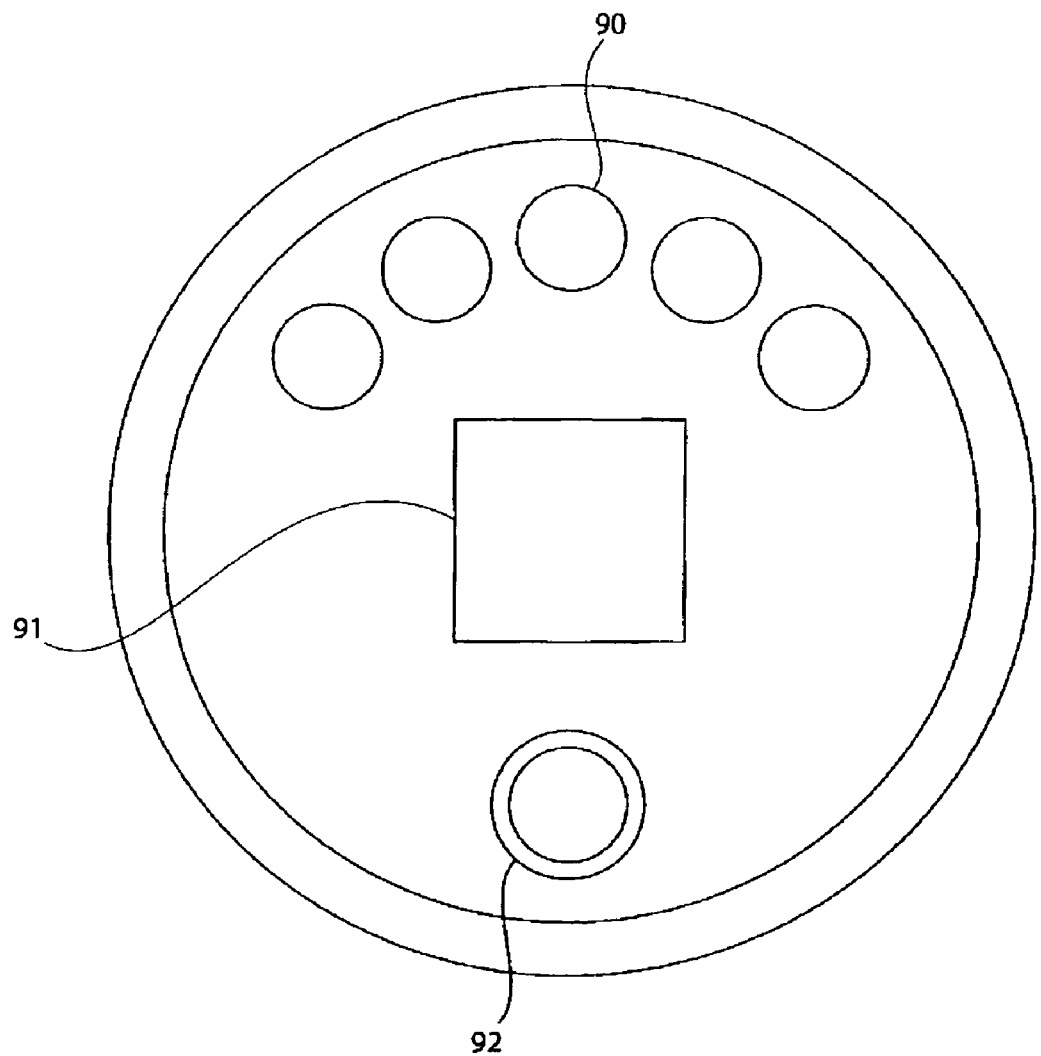
FIG. 9 illustrates a front view of a host connector receptacle with yet another variation of the preferred embodiment, with both a fibre optic interface and a waveguide interface.

An embodiment of the interface system may include electrical connections, a fibre optic connection, and a rigid or semi-rigid waveguide. A possible arrangement of a connector for use with this interface is illustrated in FIG. 9, with electrical connectors 90, a rigid waveguide connector 91 and optical fibre connection 92.

Figure 10:
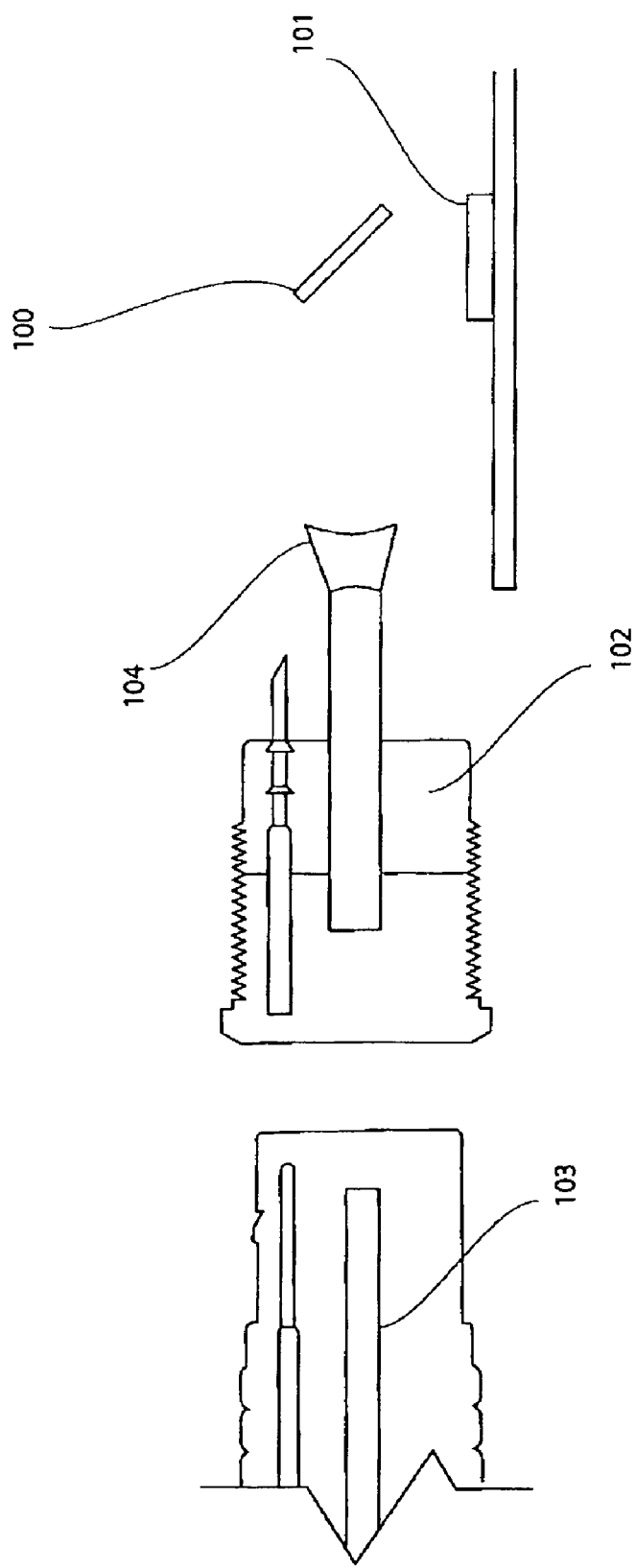
FIG. 10 illustrates a plan view of an embodiment with a waveguide interfacing to an image sensor.

FIG. 10 illustrates a plan view of a pair of connectors 102, 103 for use with an interface of the invention, including an integrated waveguide, lens system (104), and imaging device (101). The connector includes a recessed receptacle to provide alignment between the plug and receptacle. The recessed wave guide couples the light source to the connector, and transfers the received light source via a lens and mirror system (100) to an imaging array (101). By either mechanical or electrical movement of a mirror, the image sensor can receive light from the connector waveguide, or an alternative light source such as a host camera and lens system. The waveguide receptacle allows coupling to two kinds of light sources. The first is a rigid or semi-rigid waveguide constructed of a solid material such as glass, while the second is a fibre optic bundle where each fibre optic cable represents a single pixel of data. The use of a flexible fibre-optic bundle supports flexible cables of the type which may be employed by optical devices such as endoscopes.

The interface system of the invention is especially suited to medical connections, where a robust push-pull style connection is used in combination with a field programmable gate array and associated electronics to interface to a variety of different probes. The embodiments described include systems with electrical only connections, electrical plus fibre optic connections, and electrical plus fibre optic plus waveguide connections.

A new sensor unit can be developed and connected to the host system by providing a configuration file for the host detailing the serial interface method, protocol, and speed. The message channel allows negotiation between the host and a new sensor unit, with the host able to determine if a new interface configuration is required, and if required the host is able to load an appropriate configuration file. The configuration file typically programs a new configuration into a field programmable gate array (FPGA) on the host side of the interface. The flexibility of the system allows any new sensor unit development to include implementation of a new interface method.

It should be noted that where the medical field is mentioned, this includes veterinary as well as human medicine.

Although the invention has been herein shown and described in what is conceived to be the most practical and preferred embodiment, it is recognised that departures can be made within the scope of the invention, which is not to be limited to the details described herein but is to be accorded the full scope of the appended claims so as to embrace any and all equivalent devices and apparatus.

The claims defining the invention are as follows:

1. An interface system providing a communications interface between a processing unit and one or more sensor units including a first interface termination unit integrated with the processing unit, a second interface termination unit integrated with the sensor unit;
   a message channel being a communications channel carrying message data at a first data rate between the processing unit and the sensor unit,
   said message channel being active at least at substantially all times that the processing unit is active, a data channel being a communications channel carrying sensor data at a second data rate connecting the first and second interface termination units;
   said data channel being active substantially only when sensor data is required to be transmitted from the sensor unit to the processing unit; said second data rate being greater than said first data rate wherein the first interface termination unit is reconfigured in use to use a communication protocol and data rate appropriate for the sensor unit, this reconfiguration being triggered by information received from the sensor unit via the message channel.

2. The interface system of claim 1 wherein the first interface termination unit is reconfigured by the processing unit.

3. The interface system of claim 1 wherein data required to reconfigure the first interface termination unit is provided from the sensor unit.

4. The interface system of claim 1 wherein the message channel is an I2C channel.

5. The interface of claim 1 wherein the data channel employs low voltage differential signaling.

6. The interface system of claim 1 wherein the message channel is a wireless communications channel.

7. The interface system of claim 1 wherein the data channel is a wireless communications channel.

8. The interface system of claim 1 further including an optical waveguide connecting an optical probe in the sensor unit to an image sensor integrated with the processing unit.

9. The interface system of claim 1 wherein the sensor unit is a medical diagnostic probe.

10. The interface system of claim 9 wherein the sensor unit is selected from an ultrasound transducer, an endoscope, an auscultation transducer, and an otoscope.

* * * * *